United States Patent [19]

Woulfe et al.

[11] Patent Number: 5,338,864
[45] Date of Patent: Aug. 16, 1994

[54] HEXADENTATE LIGANDS USEFUL IN RADIOGRAPHIC IMAGING AGENTS

[75] Inventors: Steven R. Woulfe, Ballwin; Raghavan Rajagopalan, Maryland Heights, both of Mo.

[73] Assignee: Mallinckrodt Medical, Inc., St. Louis, Mo.

[21] Appl. No.: 909,377

[22] Filed: Jul. 6, 1992

[51] Int. Cl.⁵ ............... C07D 307/30; C07D 307/32; C07D 407/12; C07F 9/00

[52] U.S. Cl. ................... 549/207; 549/218; 549/370; 549/473

[58] Field of Search ............... 549/207, 218, 370, 473

Primary Examiner—C. Warren Ivy
Assistant Examiner—A. A. Owens
Attorney, Agent, or Firm—Brian K. Stierwalt

[57] ABSTRACT

The present invention relates particularly to novel pre-organized hexadentate ligands that are suitable for complexing with a radionuclide, and are useful as general imaging agents for diagnostic purposes.

3 Claims, No Drawings

HEXADENTATE LIGANDS USEFUL IN RADIOGRAPHIC IMAGING AGENTS

BACKGROUND OF THE INVENTION

The present invention relates to novel ligands for forming radionuclide complexes, new complexes incorporating such ligands, processes for preparing such complexes, imaging agents incorporating such complexes, and methods of imaging using such imaging agents.

The use of radiographic imaging agents for visualizing skeletal structures, organs, or tissues, is well known in the area of biological and medical research and diagnostic procedures. The procedure whereby such imaging is accomplished, generally involves the preparation of radioactive agents, which, when introduced to the biological subject, are localized in the specific skeletal structures, organs or tissues to be studied. The localized radioactive agents may then be traced, plotted or scintiphotographed by radiation detectors, such as, traversing scanners or scintillation cameras. The distribution and relative intensity of the detected radioactive agents indicates the position of the tissue in which the agent is localized, and also shows the presence of aberrations, pathological conditions or the like.

In general, the radiographic imaging agents comprise radionuclide-labelled compounds; such as complexes of technetium 99 m, rhenium 186 or rhenium 188, or other applicable radionuclides; with appropriate carriers, and auxiliary agents, such as delivery vehicles suitable for injection into, or aspiration by, the patient, physiological buffers and salts, and the like.

DETAILED DESCRIPTION OF THE INVENTION

The present invention relates particularly to novel preorganized hexadentate ligands that are suitable for complexing with a radionuclide, and are useful as general imaging agents for diagnostic purposes. In particular the present invention relates to novel ligands having the general formula:

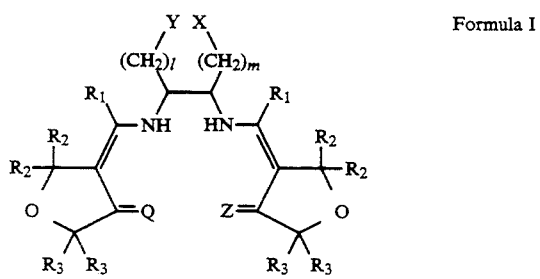

Formula I wherein $R_1$, $R_2$ and $R_3$ are the same or different and are selected from the group consisting of hydrogen, alkyl, aryl, hydroxyl, alkoxyl, mono- or poly-hydroxyalkyl, mono- or poly-alkoxyalkyl, alkoxycarbonyl or carbamoyl; l and m may be the same or different and are from 1 to 6; Q and Z may be the same or different and are an O, N or S atom; X and Y may be the same or different and are selected from the group consisting of

—OH   —$R_4$   —COOH   —COSH

-continued

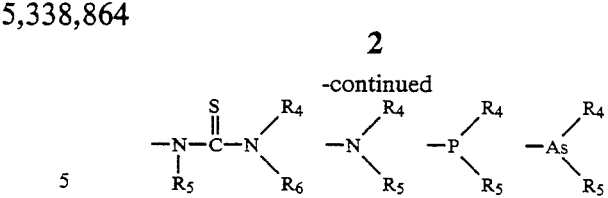

wherein $R_4$, $R_5$ and $R_6$ may be the same or different and are selected from the group consisting of hydrogen, alkyl, aryl, hydroxyl, alkoxyl, mono- or poly-hydroxyalkyl, mono- or poly-alkoxyalkyl, alkoxycarbonyl, amino, alkylamino, aminoalkyl, or carbamoyl.

In a preferred embodiment, ligands according to the present invention have the general formula (I) above, wherein $R_1$ is hydrogen; $R_2$ and $R_3$ are methyl groups; l and m are 3; Q and Z are oxygen atoms; and X and Y are the same and are as defined above. In a further preferred embodiment, X and Y are the same and are

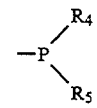

wherein $R_4$ and $R_5$ are the same or different and are selected from the group consisting of

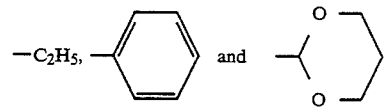

The novel ligands described above, may be incorporated into radionuclide complexes used as radiographic imaging agents. The complexes of the present invention are prepared by reacting one of the aforementioned ligands with a radionuclide containing solution under radionuclide complex forming reaction conditions. In particular, if a technetium agent is desired, the reaction is carried out with a pertechnetate solution under technetium 99 m complex forming reaction conditions. The solvent may then be removed by any appropriate means, such as evaporation. The complexes are then prepared for administration to the patient by dissolution or suspension in a pharmaceutically acceptable vehicle.

The ligands of the present invention may be prepared from commercially available starting materials such as hydroxyethylethylenediamine, etc. by standard synthetic methods as described in the following Examples.

Radionuclide complexes according to the present invention may have the general formula:

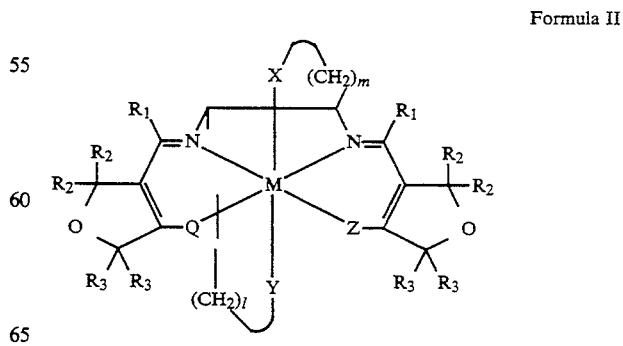

Formula II wherein M is an appropriate radionuclide such as technetium or rhenium, and wherein $R_1$-$R_3$, l, m, X, Y, Q, and Z are as defined above in formula (I). In a preferred embodiment a technetium radionuclide complex having the general formula (II) may be formed from a pertechnetate solution and a ligand having the general formula (I) above, wherein $R_1$ is hydrogen, $R_2$ and $R_3$ are methyl groups, l=3, m=3, Q=0, Z=0, and wherein X and Y are the same and are as defined above.

The radionuclide containing solution may be obtained from radionuclide generators in a known manner. For example, when forming a technetium complex, the pertechnetate solution may be obtained from a technetium generator in a known manner. The radionuclide complex forming reaction is then carried out under appropriate reaction conditions. For example, the technetium 99 m complex forming reaction is carried out under technetium complex forming temperatures, e.g. 20° C. to 100° C. for 10 minutes to several hours. A large excess of the appropriate ligands over the radionuclide complex forming amounts is preferably used. For example, when forming a technetium complex, at least a ten fold excess of the ligands over the pertechnetate solution is used. The pertechnetate is used in technetium complex forming amounts, e.g. about $10^6$ to $10^{12}$ molar amounts.

The present invention also relates to imaging agents containing a radionuclide complex as described above, in an amount sufficient for imaging, together with a pharmaceutically acceptable radiological vehicle. The radiological vehicle should be suitable for injection or aspiration, such as human serum albumin; aqueous buffer solutions, e.g. tris(hydromethyl) aminomethane (and its salts), phosphate, citrate, bicarbonate, etc; sterile water; physiological saline; and balanced ionic solutions containing chloride and or dicarbonate salts or normal blood plasma cations such as $Ca^{+2}$, $Na^+$, $K^+$, and $Mg^{+2}$.

The concentration of the imaging agent according to the present invention in the radiological vehicle should be sufficient to provide satisfactory imaging, for example, when using an aqueous solution, the dosage is about 1.0 to 50 millicuries. The imaging agent should be administered so as to remain in the patient for about 1 to 3 hours, although both longer and shorter time periods are acceptable. Therefore, convenient ampules containing 1 to 10 ml of aqueous solution may be prepared.

Imaging may be carried out in the normal manner, for example by injecting a sufficient amount of the imaging composition to provide adequate imaging and then scanning with a suitable machine, such as a gamma camera.

The complexes according to the present invention may be prepared in accordance with the examples set forth below.

EXAMPLE 1

Preparation of ligand 3c below

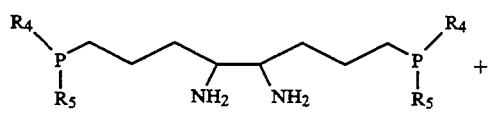

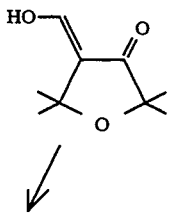

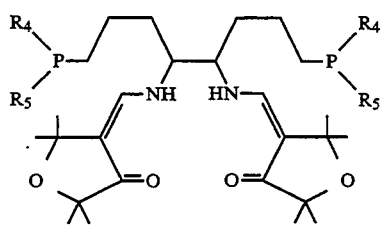

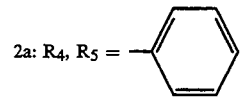 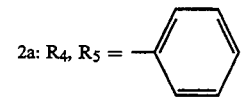

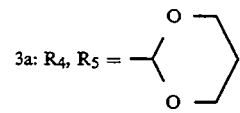 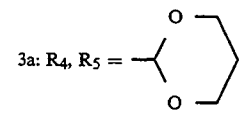

To the diphosphinodiamine 1c (1.75 g, 2.63 mmol) in methanol (25 ml) was added the furanone 2 (0.9 g, 5.3 mmol) and the reaction was warmed to 50° C. and stirred for one hour. Concentration afforded a viscous yellow oil. The material was recrystallized by first dissolving the crude oil in ether (15 ml) and adding cold pentane. Then the cloudy mixture was allowed to slowly evaporate over six hours (to approximately ⅓ volume) to afford 1.22 g (70%) of the ligand 3c as a slightly yellow powder. $^1$H-NMR (benzene-d$_6$): δ9.21 (bs, 2H), 6.22 (s, 2H), 4.47 (t, 5.5 Hz, 4H), 3.83 (dd, J=5.5, 11.7 Hz, 8H), 3.36 (t, J=11.5 Hz, 8H), 2.24 (bs, 2H), 1.05–2.00 (complex m, 18H), 1.52 (s, 12H), 1.50 (s, 12H), 1.05–1.48 (14H), 0.68 (d, J=11.7 Hz, 4H).

$^{13}$C-NMR (benzene-d$_6$): δ204.2 (s), 147.4 (d), 109.2 (s), 102.9 (CH(OCH$_2$CH$_2$CH$_2$O), Jpccc=12.7 Hz), 81.6 (s), 79.1 (s), 67.0 (CH$_2$O), 64.3 (CHNH, 33.7 (NHCHCH$_2$, Jpccc=10.8 Hz), 33.1 (CH$_3$), 33.0 (CH$_3$), 32.2 (CHCH$_2$ of dioxanylethyl group, Jpcc=13.5 Hz), 28.0 (NHCHCH$_2$CH$_2$, JPCC=12.2 Hz), 27.5 (CH$_3$), 27.3 (CH$_3$), 26.3 (OCH$_2$CH$_2$CH$_2$O), 22.6 (NHCHCH$_2$CH$_2$CH$_2$P, Jpc=14.4 Hz), 21.4 (CHCH$_2$CH$_2$ of dioxanylethyl group, Jpc=12.9 Hz).

$^{31}$P-NMR (benzene-d$_6$): δ−32.2. MS (HRFAB) m/z=969.5686 (m+1); (969.5733 calc'd for C$_{50}$H$_{86}$N$_2$O$_{12}$P$_2$).

EXAMPLE 2

Preparation of technetium 99-m complex of the ligand 3c

Sodium α-glucoheptonate (2.1 mg) was dissolved in 0.7 ml of water in a 10 ml serum vial, followed by deaeration of the solution with argon for fifteen minutes. Stannous chloride (10 μl of a 3 mg/ml solution in ethanol) was added and the vial was sealed and crimped.

Deaerated Tc-99 m generator eluent (0.3 ml) was then added to the vial via syringe to effect labelling of the glucoheptonate ligand. A solution of ligand 3c (13.8 mg in 0.5 ml ethanol) was deaerated with argon for fifteen minutes. This solution was then added to the above Tc (V) O-glucoheptonate preparation via syringe, followed by heating for fifteen minutes at 100° C. The final product was purified by dilution of the mixture to 10 ml with water, passage through an activated c-18 SepPak, washing of the SepPak with 10 ml 35/65 $CH_3CN/H_2O$ (0.05M $NH_4OAc$), and elution of the product from the SepPak with 1 ml absolute ethanol.

What is claimed is:

1. A ligand useful in forming radionuclide complexes, said ligand having the general formula:

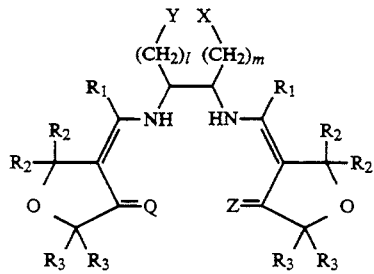

wherein $R_1$, $R_2$ and $R_3$ are the same or different and are selected from the group consisting of hydrogen, alkyl, phenyl, hydroxyl, alkoxyl, mono- or poly- hydroxyalkyl, mono- or poly- alkoxyalkyl, alkoxycarbonyl or carbamoyl; l and m may be the same or different and are from 1 to 6; Q and Z may be the same or different and are an O, N or S atom; X and Y may be the same or different and are selected from the group consisting of

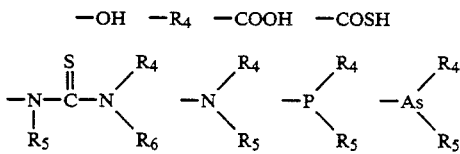

wherein $R_4$, $R_5$ and $R_6$ may be the same or different and are selected from the group consisting of hydrogen, alkyl, phenyl, hydroxyl, alkoxyl, mono- or poly- hydroxyalkyl, mono- or poly- alkoxyalkyl, alkoxycarbonyl, amino, alkylamino, aminoalkyl, or carbamoyl.

2. A ligand according to claim 1, wherein $R_1$ is hydrogen; $R_2$ and $R_3$ are methyl groups; l and m are 3; and Q and Z are oxygen atoms.

3. A ligand according to claim 1, wherein $R_1$ is hydrogen; $R_2$ and $R_3$ are methyl groups; l and m are 3; Q and Z are oxygen atoms; and X and Y are the same and are

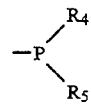

wherein $R_4$ and $R_5$ are the same or different and are selected from the group consisting of

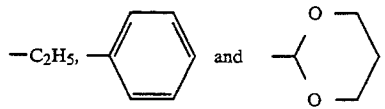

* * * * *